(12) United States Patent
Shine, Jr. et al.

(10) Patent No.: US 9,228,993 B2
(45) Date of Patent: Jan. 5, 2016

(54) METHOD OF MEASURING SHEAR BOND STRENGTH OF CEMENT

(71) Applicant: Baker Hughes Incorporated, Houston, TX (US)

(72) Inventors: Joseph Michael Shine, Jr., Spring, TX (US); Virgilio C. Go Boncan, Spring, TX (US); Robert Martin, Spring, TX (US); Keith Lant, Conroe, TX (US); Charles C. Buford, Jr., The Woodlands, TX (US)

(73) Assignee: Baker Hughes Incorporated, Houston, TX (US)

( * ) Notice: Subject to any disclaimer, the term of this patent is extended or adjusted under 35 U.S.C. 154(b) by 423 days.

(21) Appl. No.: 13/723,456

(22) Filed: Dec. 21, 2012

(65) Prior Publication Data

US 2014/0174192 A1 Jun. 26, 2014

(51) Int. Cl.
*G01N 3/00* (2006.01)
*G01N 33/38* (2006.01)

(52) U.S. Cl.
CPC .................................... *G01N 33/383* (2013.01)

(58) Field of Classification Search
CPC ................................ G01N 3/00; G01N 33/38
USPC ............................................................ 73/803
See application file for complete search history.

(56) References Cited

U.S. PATENT DOCUMENTS

| | | | | |
|---|---|---|---|---|
| 3,382,935 | A * | 5/1968 | Watts | 175/313 |
| 7,380,466 | B2 * | 6/2008 | Deeg | 73/803 |
| 7,478,790 | B2 * | 1/2009 | Yun | 248/624 |
| 8,656,788 | B2 * | 2/2014 | Jeong et al. | 73/815 |

OTHER PUBLICATIONS

L.G. Carter, G.W. Evans; "A Study of Cement-Pipe Bonding"; Journal of Petroleum Technology; SPE164; Feb. 1964; pp. 157-161; Haliburton; Duncan, Oklahoma.

George W. Evans, L. Gregory Carter; "Bonding Studies of Cementing Compositions to Pipe and Formations"; Southwestern District, API Division of Production; Mar. 1962; pp. 72-79; Haliburton; Duncan, Oklahoma.

(Continued)

*Primary Examiner* — Lisa Caputo
*Assistant Examiner* — Octavia Hollington
(74) *Attorney, Agent, or Firm* — John Wilson Jones; Jones & Smith, LLP

(57) ABSTRACT

An apparatus for determining shear bond strength of a cement to be set within a wellbore penetrating a subterranean formation consists of a housing, a vertical rod which extends from the uppermost portion of the housing through the lowermost portion of the housing, a base plate for positioning onto the bottom of the housing and for supporting the lowermost portion of the vertical rod, and a test plate for positioning onto the top of the housing through which the uppermost portion of the vertical rod extends. The apparatus may further contain a push rod. Shear bond strength is determined by introducing into the housing a sample core of the formation prior to introduction of a slurry containing the cement. The force required to break the bond between the vertical rod and the set cement may be used to determine the shear strength between the casing within the wellbore and the set cement when the cement is hardened within the wellbore. The force required to break the bond between the set cement and the sample core may be used to determine the shear strength between the set cement and formation core when the cement is hardened within the wellbore.

29 Claims, 5 Drawing Sheets

(56) References Cited

OTHER PUBLICATIONS

D. L. Sutton, K.M. Ravi; "Low-Rate Pipe Movement During Cement Gelation to Control Gas Migration and Improve Cement Bond"; SPE 22776; Oct. 1991; pp. 165-174; Society of Petroleum Engineers; Dallas, Texas.

James E. Griffith, Sameul Osisanya; "Thickness Optimization of Drilling Fluid Filter Cakes for Cement Slurry Filtrate Control and Long-Term Zonal Isolation"; SPE 29473; Apr. 1995; pp. 301-308; Society of Petroleum Engineers; Oklahoma City, Oklahoma.

Rudi Rubindini R.S.; "New Additive for Improving Shearbond Strength in High Temperature and Pressure Cement"; IADC/SPE 62750; Sep. 2000; pp. 1-18; Society of Petroleum Engineers; Kuala Lumpur, Malaysia.

H.K.J. Ladva, B. Craster, T.G.J. Jones, G. Goldsmith, D. Scott; "The Cement-to-Formation Interface in Zonal Isolation"; IADC/SPE 88016; pp. 1-14; Sep. 2004; Schlumber Cambridge Research; Kuala Lumpur, Malaysia.

Arvind D. Patel, J. Michael Wilson, Bill W. Loughridge,; "Impact of Synthetic-Based Drilling Fluids on Oilwell Cementing Operations"; SPE 50726; pp. 1-14; Feb. 1999; Society Petroleum Engineers; Houston, Texas.

Yong Ma, Maorong Cui, Xiaoyang Buo, Qing Shi, Lili Cnnoc; "How to Evaluate the Effect of Mud Cake on Cement Bond Quality of Second Interface:?"; SPE/IADC 108240; pp. 1-6; Oct. 2002; Society Petroleum Engineers; Cairo, Egypt.

\* cited by examiner

METHOD OF MEASURING SHEAR BOND STRENGTH OF CEMENT

FIELD OF THE INVENTION

The invention relates to an apparatus for measuring the shear bond strength of a set cement to the face of a subterranean reservoir and to the face of the casing within the wellbore of the reservoir. The invention further relates to methods of using the testing apparatus and to methods of optimizing performance-based parameters in field operations.

BACKGROUND OF THE INVENTION

During construction of oil and gas wells, a rotary drill is typically used to bore through subterranean reservoirs of the earth to form a wellbore. As the rotary drill bores through the earth, a drilling fluid or mud is circulated through the wellbore. Drilling fluids are usually pumped from the surface into the wellbore through a drill string and transmitted to the drill bit. By continuously pumping the drilling fluid, the drilling fluid can be circulated out the bottom of the drill pipe and back up to the well surface through the annular space between the wall of the wellbore and the drill pipe.

Once the wellbore has been drilled, casing is lowered into the wellbore. A cement slurry is then pumped into the casing and a plug of fluid, such as drilling mud or water, is then pumped behind the cement slurry in order to force the cement up into the annulus between the exterior of the casing and the borehole. The cement slurry is then allowed to harden as a sheath. The cement sheath then holds the casing in place. The well is subsequently stimulated in order to enhance the recovery of oil or gas from the reservoir.

Maintaining zonal isolation for the lifetime of the well is critical. Leakage behind the casing reduces the cost-effectiveness of the well and may cause safety risks from pressure build-up. During well treatment operations, in particular completion and production phases of the well, variations in temperature and internal pressure of the wellbore pipe string may result in radial and longitudinal pipe expansion and/or contraction. This tends to place stress on the annular cement sheath existing between the outside surface of the pipe string and the inside formation surface or wall of the wellbore. Such stresses lead to cracking and/or disintegration of the cement sheath. Thus, failure of a cement sheath to provide zonal isolation may occur as a result of properties of the cement-casing interface, the cement-formation interface as well properties of the cement.

It has become increasingly important for service providers to provide to well operators cement mixes capable of withstanding specific downhole conditions well and specific operating conditions which the well is to be subjected.

Not only must the cement slurry containing such cement mixes exhibit a pumpable viscosity, acceptable fluid loss control, minimal settling of particles and the ability to set within a practical time, the cement mix and the properties of the cement slurry must be carefully selected in order to minimize or eliminate cracking of the cement when set as a cement sheath. As such, the cement mix and the slurry containing the mix must be tailored in order for the set cement to withstand those axial stresses, shear stresses and compressional stresses encountered under in-situ wellbore conditions. Further, the components of the cement mix and the cement slurry must be selected such that, when hardened, the set cement is not brittle since brittleness causes cracking of the sheath.

Knowledge of the bond strength of the cement sheath at the formation face and at the casing interface at in-situ downhole conditions would be an invaluable tool to ensure an optimal cement mix and job design are provided to the well operator. To date, however, neither a testing protocol nor an apparatus has been developed which is capable of measuring shear bond strength at both interfaces.

A testing method is needed for evaluating cement mixes and in particular the shear bond strength of a cement set from such mixes under conditions which simulate conditions found in a wellbore environment. The method needs to provide reliable and reproducible data at both the formation interface and at the casing interface. In particular, a testing protocol is desired for assessing bond strength at both the formation interface and at the casing interface which is based on a targeted subterranean formation to be cemented and bottom hole conditions of the well. Testing methods under these conditions will provide the requisite data for optimizing the properties of cementitious slurries for rendering suitable hardened cements at in-situ stress conditions.

SUMMARY OF THE INVENTION

The testing apparatus described herein may be used to determine the integrity of a set cement to the face of a subterranean formation as well as the integrity of the set cement to the casing.

Cement mixes may be evaluated for a subterranean formation from which fluids are to be produced ("a targeted formation") or zones isolated using the testing apparatus described herein. The testing apparatus may be used to determine the shear bond strength of a cement set from a cementitious slurry which contains the cement mix and job design being evaluated.

In one embodiment, the shear bond strength between the casing of the wellbore and a sheath set from a cementitious slurry containing a cement mix may be determined using the testing apparatus described herein.

In another embodiment, the shear bond strength between a cement sheath and a subterranean formation may be evaluated using the testing apparatus described herein.

The apparatus provides the ability to evaluate a cement mix hardened within a confined targeted subterranean formation or zone prior to pumping a slurry containing the cement mix into an annular gap between the formation and/or casing. In particular, the apparatus provides the ability to evaluate the shear bond strength between the cement sheath (hardened from the cement mix being evaluated) and the casing within the wellbore of the targeted formation. In addition, the apparatus provides the ability to evaluate the shear bond strength between the cement sheath (hardened from the cement mix) and the targeted formation itself.

In an embodiment, the testing apparatus consists of a circular housing, a vertical rod which extends from the uppermost portion of the housing through the lowermost portion of the housing, a base plate for positioning onto the lower end of the housing and for supporting the lowermost portion of the vertical rod, and a test plate having a central opening through which the vertical rod may extend. In a preferred embodiment, one side of the test plate is flat and the other side of the test plate has a recessed area encircling the central opening. Both sides of the base plate are flat; the exterior being solid and the interior side having a recessed area for receiving the lower end of the vertical rod.

In another embodiment, the testing apparatus consists of a circular housing, a vertical rod which extends from the uppermost portion of the housing through the lowermost portion of the housing, a base plate for positioning onto the lower end of the housing and for supporting the lowermost portion of the vertical rod during the setting of the cementitious slurry, a push rod, and a test plate having a central opening through which the vertical rod may extend, one side of the test plate being a flat surface and the other side of the test plate having a recessed cavity onto which a sample core of the targeted formation may rest during testing.

In an embodiment, the shear bond strength of a cement sheath may be measured by introducing a cementitious slurry containing a cement mix into the testing apparatus wherein a sample core of a targeted formation is within the testing apparatus and wherein the slurry is introduced into the annulus, defined as the area between the core and a vertical rod which extends from the top of a housing to the bottom of the housing. During testing a base plate is positioned onto the bottom of the housing, the lowermost portion of the vertical rod resting within a recessed area of the interior surface of the base plate, the exterior surface of the base plate being flat. A first test plate having a central opening and a flat surface is further positioned onto the top of the housing. The testing apparatus is sealed and then subjected to temperatures and/or pressures to set the cement. The base plate and test plate are then removed from the bottom and top of the housing. The first test plate is then placed on the bottom of the housing with the flat surface facing the set cement. Pressure is then applied to the top of the vertical rod. The force required to break the bond between the vertical rod and the set cement is measured. The shear bond strength between the vertical rod and the set cement is determined by dividing the measured force by the contact area of the vertical rod.

The shear bond strength between the cement sheath and the targeted formation may further be determined by removing the base plate and the test plate from the bottom and top of the housing, respectively, and then securing to the bottom of the housing a second test plate having a central opening and having a recessed area approximating the outer circumference of the core. The second test plate has a central opening for passing the lower end of the vertical rod there through. The second test plate also as a recessed area. The diameter of the recessed area is such that the sample core may fit within the recessed area. A push rod may then be installed over the top of the vertical rod. Pressure may then be applied onto the push rod and the force required to break the bond between the set cement and the sample core is measured. The shear bond strength is then determined by dividing the measured force by the contact area of the vertical rod. In a preferred embodiment, first test plate and the second test plate are the one and the same wherein one surface of the plate has a flat surface and the other surface of the plate contains the recessed area for receiving the sample core.

Methods of using the testing apparatus employ a sample core of the targeted subterranean formation and simulate the equivalent spacing existing in-situ between the formation and annulus of a producing well. As such, use of the testing apparatus allows for an accurate measurement of shear bond strength at the actual interface of cement and formation as well as at the actual interface of cement and casing within the producing well of interest.

The slurry placed in the apparatus can be cured at simulated bottom hole conditions including temperature and pressure.

BRIEF DESCRIPTION OF THE DRAWINGS

In order to more fully understand the drawings referred to in the detailed description of the present invention, a brief description of each drawing is presented, in which.

DETAILED DESCRIPTION OF THE PREFERRED EMBODIMENTS

Figure 1:
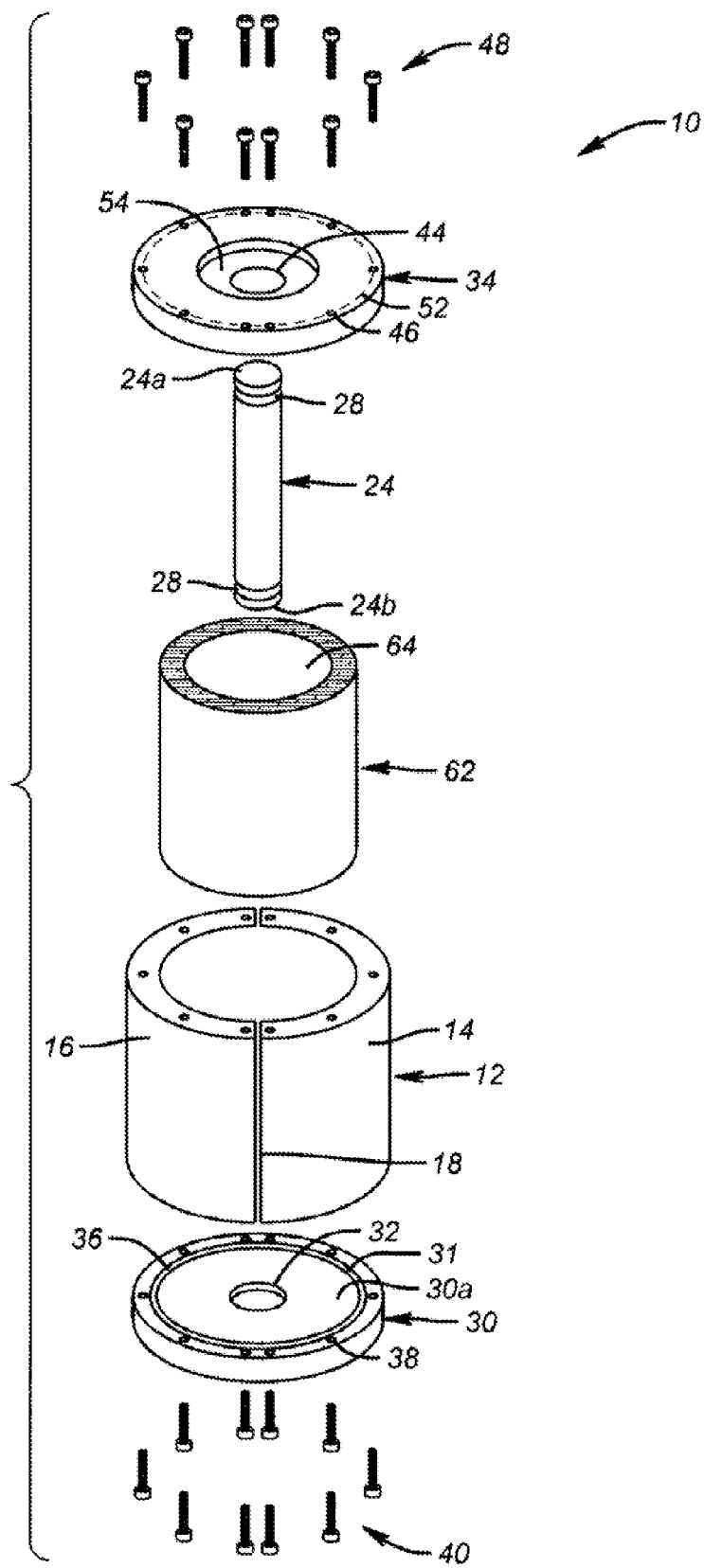
FIG. 1 represents an exploded view of an exemplary testing apparatus for measuring shear bond strength at the interface of the cement and vertical rod as well as at the interface of sample formation core to cement.

The testing apparatus, as illustrated in FIG. 1, contains circular housing 12. During testing, the sample core of a subterranean formation and a cementitious test slurry are contained within a circular housing. In a preferred embodiment housing 12 is composed of multiple body units. FIG. 1 illustrates two body units 14 and 16 of approximately the same dimensions. During testing, the use of multiple body units facilitates placement of the sample core into the housing to ensure a tight fit of the sample core within the housing. The ends of the body units may be secured together by one or more fasteners 18, such as hose clamps. The inside diameter of the circular housing may be between from about 1.25 to about 5 inches.

Figure 2:
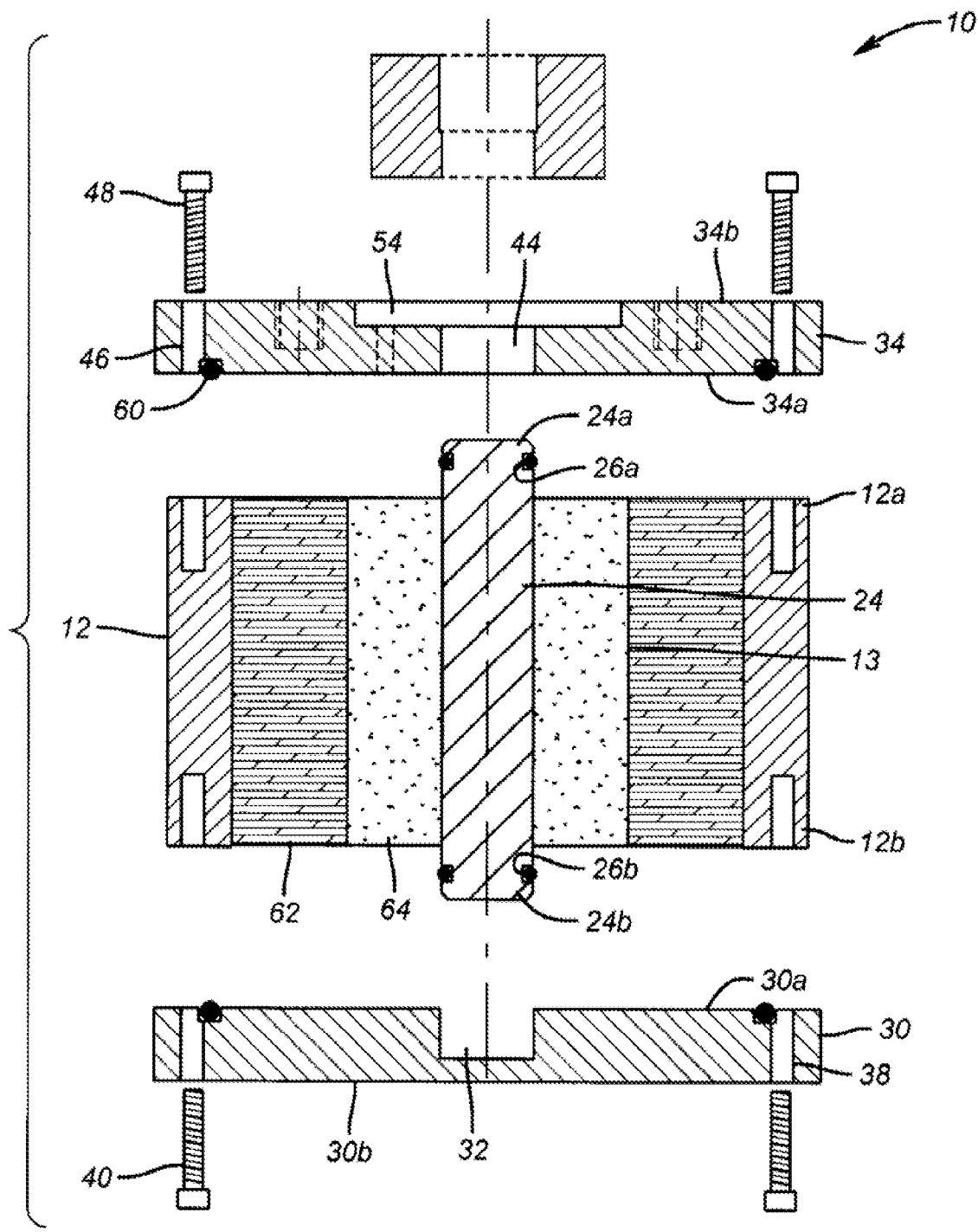
FIG. 2 depicts a cross-sectional view showing the spatial arrangement of the vertical rod, sample core, base plate, test plate, and cement sheath during testing of shear bond strength at the interface of sample core to cement.

During curing, testing apparatus 10 further contains vertical rod 24 within the interior of housing 12. The diameter of the vertical rod may be between from about 0.5 to about 1.0 inches. As illustrated in FIG. 2, the length of vertical rod 24 extends through the uppermost portion 12a of housing 12 and through the lowermost portion 12b of housing 12. Receptor grooves 26a and 26b are preferably located in the upper end 24a and lower end 24b of vertical rod 24, respectively. During testing, O-rings 28 may be placed into receptor grooves 26a and 26b, respectively.

Testing apparatus 10 further contains base plate 30 and test plate 34. During testing, interior surface 30a of base plate 30 is placed against the lowermost portion 12b of housing 12 and supports housing 12. As illustrated in FIG. 2, interior surface of base plate 30 has recessed area 32 for receiving lower end 24b of vertical rod 24. The interior surface of base plate 30 further preferably has a circular recessed groove along its inside perimeter for receiving a rubber strip or O-ring 31. Exterior surface 30b of base plate 30 is solid. Base plate 30 further has one or more openings 38 for receiving fasteners 40 (shown as bolts) for securing base plate 30 to housing 12.

Test plate 34 has central opening or through-hole 44 for extending vertical rod 24 therethrough. Test plate 34 further contains openings 46 along its inner perimeter for fasteners 48 for securing test plate 34 to upper housing 12a. FIG. 2 shows test plate 34 having a flat interior surface 34a and an exterior surface 34b having recessed cavity 54. Recessed cavity 54 is of a diameter sufficient for receiving the sample core of the formation during testing.

During curing of the cementitious slurry, interior flat surface 34a of test plate 34 is placed to face the inside of housing 12. Interior surface 34a of test plate 34 further has recessed groove 52 along its inner perimeter for receiving O-ring 60.

FIG. 2 shows different surfaces for the exterior face and the interior face of test plate 34. This enables the same plate to be used in the testing of shear bond strength between both the casing to cement sheath as well as the cement sheath to formation core. Interior surface 34a having a flat surface may be used by being placed inwards toward the set cement during testing of the bond strength between the set cement and vertical rod. Exterior surface 34b having recessed cavity 54 surrounding central opening 44 may be used by being placed inwards toward the set cement during testing of the bond strength between the set cement and sample core. The indentation of recessed cavity 54 is such that during testing push rod 56 may be placed over upper end 24a of vertical rod 24 through through-hole 57. Force is then applied to push rod 56.

Test plate 34 has been described as having two distinct surfaces—one surface being the other surface having recessed cavity having a diameter such that the sample of set cement may be fitted within the recessed cavity during testing of bond strength between the set cement and the sample core. This is an advantageous design for test plate since it minimizes the number of parts required to complete testing. However, in some circumstances, it may be desirable to have two plates wherein one plate has the flat surface and a second plate having recessed cavity for acceptance of the sample core. Test plate 34 has been described herein as having a distinct interior and a distinct exterior surface. This is not necessary since two different plates may be used. Where shear bond strength between the vertical rod and cement sheath and shear bond strength between the core and cement sheath are both being determined, use of cover 34 having exterior surface 34b and interior flat surface 34a is desired since it minimizes the number of elements required to constitute the testing apparatus. However, test plate 34 may consist of a plate with central opening 44 and two flat surfaces for use in the testing of shear bond strength between vertical rod 24 and the cement sheath, such as when only testing is desired between the vertical rod and the cement sheath. A separate test cover may be used having a recessed cavity on one or both sides of the test cover if testing is only desired for the shear bond strength between the cement sheath and the sample core.

The shear bond strength between a set cement and a sample core of a targeted subterranean formation as well as the shear bond strength between a set cement and the casing within the wellbore penetrating the formation may be determined using testing apparatus 10. Testing is conducted by placing within the interior of housing 12 a sample core of the formation. The testing method provides accurate data since the core of the targeted formation is used. As illustrated in FIG. 1, sample core 62 is placed along the inner perimeter of housing 12.

Figure 3:
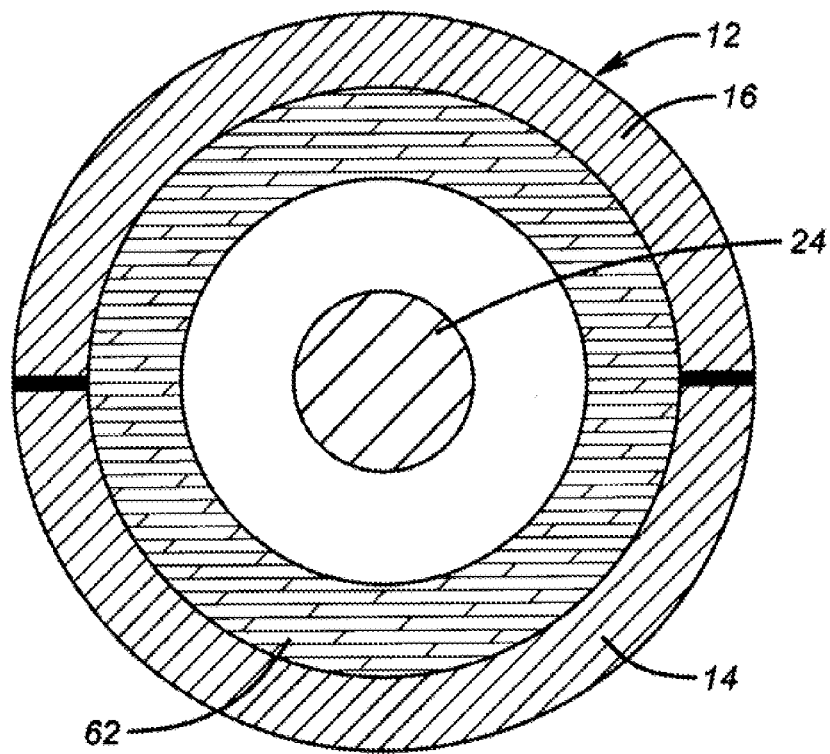
FIG. 3 depicts a top view of the housing of the testing apparatus having sample core and cement sheath.

Prior to assembly of testing apparatus 10, it is desirable to first determine the diameter of sample core 62, the diameter of vertical rod 24 and the length of vertical rod 24. FIG. 3 is a representative cross-sectional view of sample core 62 in housing 12 wherein the outer diameter (OD) of the sample core is illustrated to be 4 inches and the inner diameter (ID) of the formation sample core (the diameter of the core closest to the cement sheath) is shown to 2.25 inches. The wall thickness of the formation core within housing 12 is illustrated to be 0.875 inches. The inside diameter of cement sheath 64 (set cement) is illustrated to be 0.75 inches. The testing apparatus may, of course, be modified for other sizes of housings, vertical rods, samples cores, etc.

Prior to introduction of the cement slurry into the testing apparatus, base plate 30 is placed adjacent to the lowermost portion 12b of housing 12. Base plate 30 may then be secured to housing 12. Preferably portions of O-ring 36 for placement into the recessed groove surrounding the interior of base plate 30 are first lubricated. O-rings 28 are further preferably lubricated and placed into O-ring receptor grooves 26a and 26b of vertical rod 24. Vertical rod 24 is then installed into housing, the lower end 24b of vertical rod being inserted into recessed area 32 of base plate 30.

A rubber strip approximately $\frac{1}{16}$" to $\frac{3}{32}$" thick is placed between the interface of split body pieces 14 and 16. The width and the length of the rubber strip are about the same as the thickness and the height of the body pieces. Fasteners 40 are inserted into openings 38 on base plate 30 and into the receiving (or female) ports on the housing bottom 12b (not shown). Typically from about 5 to about 15 in/lb of torque is applied to fasteners 18 to seal split body pieces 14 and 16 together (illustrated in FIG. 1) and fasteners 40 in order to provide an air tight testing apparatus and to more tightly secure housing 12 to base plate 30.

A portion of cementitious slurry containing a cement mix to be tested is then introduced into housing 12 and onto base plate 30. Typically about $\frac{1}{5}$ to about $\frac{1}{3}$ of the interior of housing 12 is filled with the slurry. The sample core is then placed into the housing. The outer diameter of the sample core may be between from about 2 to about 6 inches, the thickness of the sample core may be between from about 0.25 to about 0.75 inches, and the inner diameter of the sample core may be between from about 2.0 to about 2.5 inches. The cementitious slurry is allowed to travel and form a circumferential u-shape in between sample core 62 and interior wall 13 of housing 12. A glass rod may be used to puddle the slurry to remove trapped air.

The area between vertical rod 24 and the interior wall of sample core 62 defines the annular space. The cement is set within the annular space to form cement sheath 64. Cementitious slurry is poured into the annular space to the top of body 12. In a preferred embodiment, the diameter of the annular gap ranges from about 0.5 to about 2 inches which is the size of a conventional annulus within a typical wellbore. The slurry poured into the annulus may then be puddled to remove air entrapped within the slurry.

After the cementitious slurry is poured into the annulus, test plate 34 is then installed over housing 12 with the interior surface 34a of test plate 34 facing inward against the slurry. Upper end 24a of vertical rod 24 extends through central opening 44 of test plate 34. Fasteners 48 are passed through openings 46 on test plate 34 and are tightened.

Testing apparatus 10 may then be submerged into a water bath maintained at a temperature between from about 180° F. to about 200° F., preferably around 190° F. After the slurry has been cured, the testing apparatus is then removed from the water bath. Typically the testing apparatus is allowed to remain in the water bath for up to 72 hours. Base plate 30 and test plate 34 are then removed.

The elements of the testing apparatus are preferably composed of a metal capable of withstanding pressures at such in-situ conditions. In a preferred embodiment, the metal is a metal alloy, such as stainless steel or another alloy containing iron.

Figure 4:
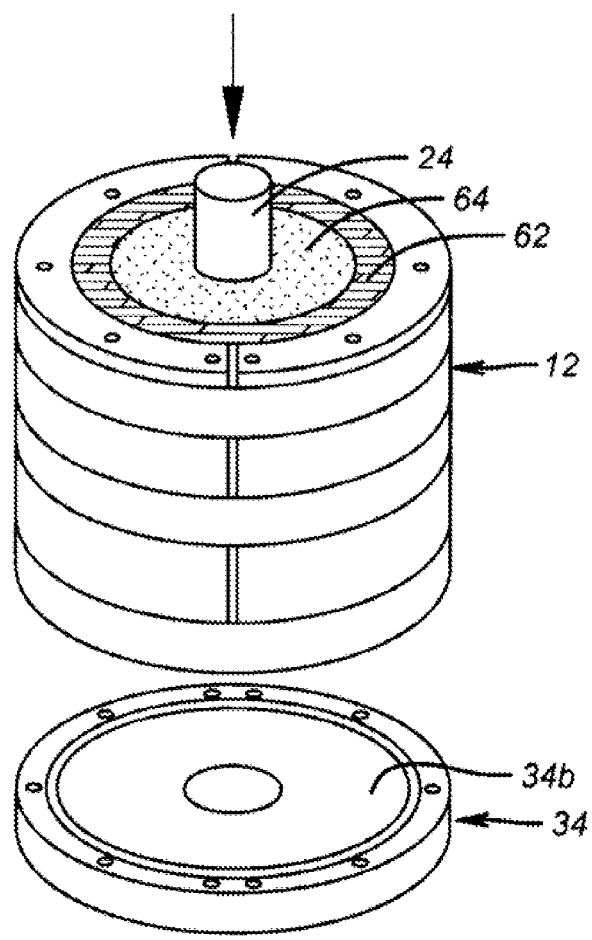
FIG. 4 represents the testing apparatus in an exemplary testing protocol for measuring the shear bond strength between a vertical rod and cement sheath. Results from this protocol are indicative of shear bond strength at the interface of cement and casing within the wellbore.

FIG. 4 depicts the setup for testing apparatus 10 for determining shear bond strength between vertical rod 24 and cement sheath 64. Test cover 34 is illustrated as being placed onto the lowermost housing portion 12b such that the flat surface 34a of test plate 34 faces the cement sheath. Thus, during the testing, test cover 34 supports the housing containing vertical rod 24, cement sheath 64, and formation core 62. After fastening and securing the test plate onto the housing, force is then applied onto the upper end 24a of vertical rod 24.

The force may be at a load rate of between from about 2,500 to about 5,000 lbs/minute, typically about 4,000 lbs/minute. The maximum force to break the bond between vertical rod 24 and cement sheath 64 is then determined. The strength of the bond (representing the shear bond between the casing within the wellbore to the cement sheath) may then be determined by dividing the maximum force by the contact area of the vertical rod (to the cement sheath).

Figure 5:
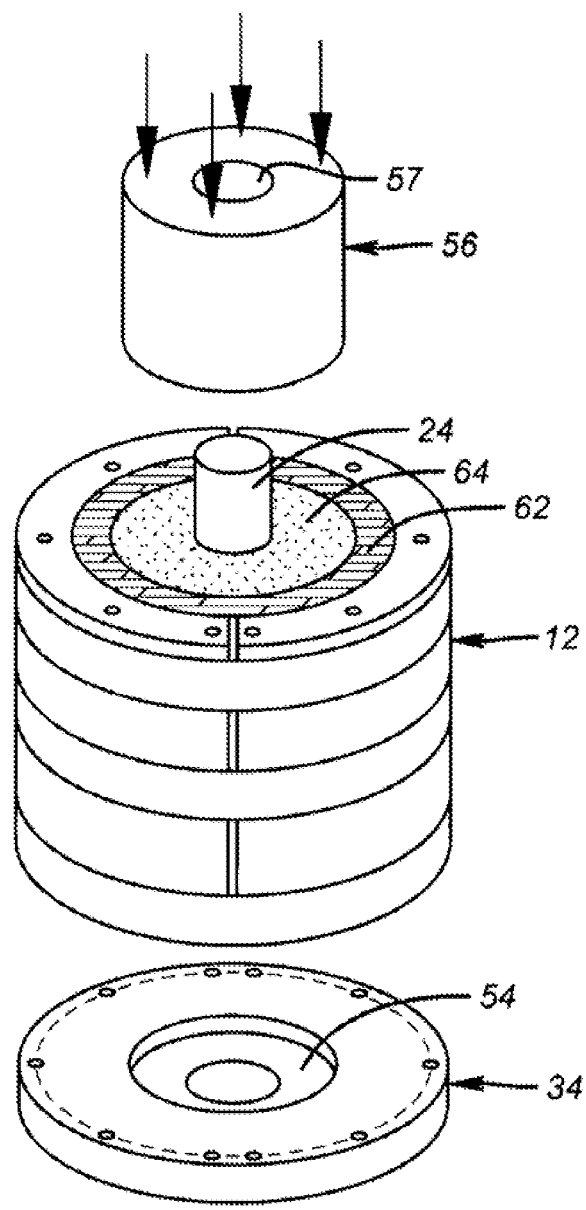
FIG. 5 represents the testing apparatus in an exemplary testing protocol for measuring the shear bond strength between cement sheath and sample core. Results from this protocol are indicative of shear bong strength at the interface of cement and formation core within the wellbore.

The shear bond strength between vertical rod 24 and cement sheath 64 may then be determined, if desired. FIG. 5 illustrates an exemplary testing protocol for measuring the shear bond strength between sample core 62 and cement sheath 64. The exploded nature of FIG. 2 shows the spatial arrangement of the elements of the apparatus during an exemplary testing protocol. This protocol may be conducted after testing of the shear bond strength between vertical rod 24 and cement sheath 64 has been concluded. Alternatively, testing of the shear bond strength between sample core 62 and cement sheath 64 may be conducted by itself, i.e., without following the protocol for the testing of the bond strength between vertical rod 24 and cement sheath 64.

As illustrated in FIG. 5, test plate 34 is placed over the lowermost housing portion 12b such that the recessed cavity 54 faces cement sheath 64 within the housing. The surface of the test plate having the flat surface 34b faces away from the cement sheath. Push rod 56 is then placed over the upper portion 24a of vertical rod 24 through through-hole 57. The inside diameter of the push rod is such that the push rod is positioned over the cement sheath without buttressing housing 12.

Force is applied to push rod 56. The amount of force required to break the bond between cement sheath 64 and the core sample 62 is determined. Typically, the amount of force applied to the push rod is between from about 3,000 lbs/min to about 5,000 lbs/min, typically about 4000 lbs/minute. Shear bond strength is then determined by dividing the maximum force by the contact area. This measurement is indicative of the shear bond strength of the cement sheath to formation core at in-situ reservoir conditions.

A benefit of testing apparatus 10 is that allows a service operator to evaluate a cement mix at in-situ conditions in the laboratory. By employing a test protocol using the a sample of actual formation core of a targeted subterranean formation to be drilled and cemented, the shear bond strength between the set cement and the casing and between the cement sheath and the formation may be determined prior to pumping of the cement slurry. Since in-situ pressure and temperature conditions may be utilized using the testing protocol described herein, a slurry containing an evaluated and then pre-selected cement mix may be pumped into the wellbore with knowledge of the stress conditions a set cement can endure at in-situ conditions.

The following examples are illustrative of some of the embodiments of the present invention. Other embodiments within the scope of the claims herein will be apparent to one skilled in the art from consideration of the description set forth herein. It is intended that the specification, together with the examples, be considered exemplary only, with the scope and spirit of the invention being indicated by the claims which follow.

EXAMPLES

Example 1

The inside diameter (CID) of a shale sample core from North Africa was measured to be 2.133 in. The outside diameter of a vertical rod (CROD) and the length of the vertical rod (CRL) were measured to be 0.75 in. and 3.78 in., respectively. Split body pieces 14 and 16 were secured to form a housing. O-ring 36 was inserted within the recessed grooves of base plate 30 and the base plate was secured to the housing after rubber gaskets and O-rings were lubricated with a moly grease. Vertical rod 24 having lubricated O-rings 28a and 28b within recessed areas was installed into the recess of base plate 30.

A cementitious slurry was prepared by mixing Portland Class G cement and fresh water at 15.8 pounds per gallon (ppg). To the slurry was mixed 35 wt. % of a 200-325 mesh silica flour; and 0.02 gallons per sack of cement (gps) of a liquid defoamer; 0.20 gps of a liquid cement dispersant; 1.46 gps of a liquid bonding agent; 0.39 gps of a liquid fluid loss control agent; and 0.10 gps of a liquid cement retarder.

About ¼ of the space within the housing was filled with the cementitious slurry. The core was then inserted into the mold. The core was rocked inside the mold in order to allow the slurry to u-tube in between the core and the mold, filling the annular space with the slurry. The annular space with the slurry was then topped off using a glass rod to puddle the slurry 30 times per API RP_10B to remove trapped air. The core was then rocked inside the mold in order to allow the slurry to u-tube in between the core and the mold. The top was then installed with the O-ring side facing the split body and each of the bolts was tightened.

A constant and uniform torque was applied to the exterior of the mold. The mold was then submerged into a water bath maintained at 190° F. The mold was then removed after about 72 hours from the water bath. The top plate and the base plate were then removed from the mold.

Casing to Cement Shear Bond Measurement.

The length of the vertical rod extending from the top plate and the length of the vertical rod extending from the base plate was measured as 0.4205 and 0.377 inches, respectively. The contact area for the vertical rod to the cement (casing) was then determined as follows:

$$\pi(CROD)(CRL-[CRTL+CRBL]); \text{ or}$$

$$\pi(0.75 \text{ in.})(3.781 \text{ in}-[0.4205 \text{ in.}+0.37716 \text{ in.}])=7.029 \text{ in}^2$$

The test plate was then installed on the bottom of the mold with the O-ring 52 seated against the split body of housing 12. The maximum force for the shear bond of the casing to cement was recorded as 2076 lbs which was obtained by applying force to the vertical rod at a load rate of 4,000 lbs/minute. The strength was the determined as follows:

$$\text{Max Force (lbs)} \div \text{Contact Area (in}^2\text{)}=\text{Strength (psi); or}$$
$$2076 \text{ lbs} \div 7.029 \text{ in}^2=295 \text{ psi}$$

Cement to Formation Shear Bond Measurement.

Test plate 42 was inverted and installed on the bottom of housing 12, previously occupied by base plate 14 with recessed cavity 54 of test plate 42 facing formation sample core 62. The contact area for the vertical rod to the inside diameter of the shale sample core was then determined as follows:

$$\pi(CID)(CRL-[CRTL+CRBL]); \text{ or}$$

$$\pi(2.133 \text{ in.})(3.781 \text{ in}-[0.4205 \text{ in.}+0.37716 \text{ in.}])=19.99 \text{ in}^2$$

Push rod 56 was then installed over vertical rod 24 at the top of the apparatus. Force was then applied to the push rod at a load rate of 4000 lbs/minute and the maximum force for the shear bond of the cement to formation was recorded as 19,291 lbs. Strength was the determined as follows:

Max Force (lbs)÷Contact Area (in$^2$)=Strength (psi); or
19,291 lbs÷19.99 in$^2$=965 psi The foregoing disclosure and description of the invention is illustrative and explanatory thereof, and various changes in the size, shape, and materials, as well as in the details of illustrative construction and assembly, may be made without departing from the spirit of the invention.

What is claimed is:

1. A method of measuring shear bond strength of a cement to be set in a wellbore penetrating a subterranean formation comprising:
   (a) introducing into a housing a cementitious slurry containing a cement mix, wherein:
      (i) a base plate is secured to the bottom of the housing;
      (ii) a vertical rod extends from the bottom of a recessed area of the base plate to the top of the housing; and
      (iii) a sample core of the subterranean formation is within a circular housing, wherein an outer wall of the sample core is adjacent to an inner wall of the housing and wherein a bottom of the sample core is adjacent to the base plate
   wherein the cementitious slurry is introduced into the housing between the vertical rod and the sample core and further wherein a portion of the cementitious slurry travels between the outer wall of the core and the inner wall of the housing;
   (b) positioning a test plate onto a top of a housing, wherein the flat surface of the test plate faces the cementitious slurry within the housing;
   (c) subjecting the apparatus to heat at a temperature and for a time sufficient for the cementitious slurry to set;
   (d) removing the base plate from the bottom of the housing and removing the test plate from the top of the housing;
   (e) positioning the test plate onto the bottom of the housing wherein the flat surface of the test place faces the set cement;
   (f) applying pressure onto the top of the vertical rod;
   (g) measuring the maximum force required to break the bond between the set cement and the vertical rod; and
   (h) determining the shear bond strength between the vertical rod and the set cement by dividing the maximum force by the surface area of the vertical rod in contact with the set cement.

2. The method of claim 1, wherein the amount of pressure applied in step (f) is between from about 3,000 to about 5,000 lbs/min.

3. The method of claim 1, wherein the outer diameter of the sample core is between from about 2 to about 6 inches.

4. The method of claim 3, wherein the thickness of the sample core is from about 0.25 to about 0.75 inches.

5. The method of claim 1, wherein the inner diameter of the sample core is between from about 2.0 to about 2.5 inches.

6. The method of claim 1, wherein cementitious slurry is introduced into the housing in step (a) in stages and wherein the first stage is introduced into the housing prior to placement of the sample core into the housing.

7. The method of claim 6, wherein from about ⅕ to about ⅓ of the total amount of the cementitious slurry introduced into the housing is introduced in the first stage.

8. The method of claim 1, further comprising:
   (i) detaching the base plate from the housing;
   (j) attaching the test plate to the bottom of the housing, wherein the surface of the test plate having the recessed cavity faces the set cement and wherein the bottom portion of the sample core rests within the recessed cavity;
   (k) placing a push rod having a central opening over the top of the vertical rod, applying pressure onto the push rod and measuring the maximum force required to break the bond between the set cement and the sample core; and
   (k) determining the shear bond strength between the set cement and the sample core by dividing the measured maximum force by the area of the vertical rod in contact with the set cement.

9. The method of claim 8, wherein the amount of pressure applied in step (k) is between from about 2,500 to about 5,000 lbs/min.

10. The method of claim 8, wherein the outer diameter of the sample core is between from about 2 to about 6 inches.

11. The method of claim 10, wherein the inner diameter of the sample core is between from about 2.0 to about 2.5 inches.

12. The method of claim 8, wherein the thickness of the sample core is from about 0.25 to about 0.75 inches.

13. A method of measuring shear bond strength of a cement to be set in a wellbore penetrating a subterranean formation, the method comprising:
   (a) introducing into a circular housing a cementitious slurry wherein:
      (i) a solid base plate is secured to the bottom of the housing;
      (ii) a vertical rod extends from the bottom of a recessed area of the inner surface of the base plate to the top of the housing; and
      (iii) a sample core of the subterranean formation is within the circular housing, the outer wall of the sample core being adjacent to the inner wall of the housing and wherein the bottom of the sample core is adjacent to the base plate
   wherein the cementitious slurry is introduced into the housing between the vertical rod and the sample core;
   (b) forming a testing apparatus by positioning a test plate onto the top of the circular housing, the test plate having a flat surface and a through-hole and wherein the upper portion of the vertical rod extends through the through-hole;
   (c) subjecting the testing apparatus to heat at a temperature and for a time sufficient for the cementitious slurry to set in the testing apparatus;
   (d) removing the test plate and the base plate from the circular housing;
   (e) applying a flat surface testing plate having a through-hole onto the bottom of the housing, the bottom of the vertical rod extending through the through-hole of the flat surface testing plate;
   (f) applying pressure onto the top of the vertical rod;
   (g) measuring the maximum force required to break the bond between the set cement and the vertical rod; and
   (h) determining the shear bond strength between the vertical rod and the set cement by dividing the maximum force by the surface area of the vertical rod in contact with the set cement.

14. The method of claim 13, wherein the test plate and the flat surface testing plate are the same.

15. A method of pre-determining the shear bond strength of a cement mix prior to pumping a cementitious slurry containing the cement mix between a pre-selected subterranean formation penetrated by a wellbore and casing within the wellbore, the method comprising:
   (a) introducing a portion of the cementitious slurry into a testing apparatus, the testing apparatus comprising:

(i) a circular housing;
(ii) a base plate having a recessed area;
(iii) a vertical rod which extends from the recessed area of the support base past the uppermost portion of the circular housing wherein a sample core of the pre-selected subterranean formation is placed between the inner wall of the circular housing and the vertical rod, the cementitious slurry being introduced into the testing apparatus between the sample core and the vertical rod;

(b) positioning a test plate onto the top of the circular housing, the test plate having an opening through which the uppermost portion of the vertical rod extends;

(c) subjecting the testing apparatus to heat at a temperature and for a time sufficient for the cementitious slurry to harden in the testing apparatus;

(d) removing the test plate and the base plate from the circular housing;

(e) applying a flat surface testing plate having a through-hole onto the bottom of the housing, the bottom of the vertical rod extending through the through-hole of the flat surface testing plate;

(f) applying pressure onto the top of the vertical rod;

(g) measuring the maximum force required to break the bond between the hardened cement and the vertical rod; and (h) determining the shear bond strength between the vertical rod and the hardened cement by dividing the maximum force by the area of the vertical rod in contact with the hardened cement wherein the shear bond strength of step (h) approximates the shear bond of the cement mix, when hardened, between the subterranean formation and the casing within the wellbore.

16. The method of claim 15, wherein the test plate and the flat surface testing plate are the same.

17. The method of claim 15, wherein the amount of pressure applied in step (f) is between from about 3,000 to about 5,000 lbs/min.

18. The method of claim 15, wherein the outer diameter of the sample core is between from about 2 to about 6 inches.

19. The method of claim 15, wherein the thickness of the sample core is from about 0.375 to about 2 inches.

20. A method of measuring shear bond strength of a cement to be set in a wellbore penetrating a subterranean formation, the method comprising:
  (a) introducing into a circular housing a cementitious slurry wherein:
    (i) a solid base plate is secured to the bottom of the housing;
    (ii) a vertical rod extends from the bottom of a recessed area of the inner surface of the base plate to the top of the housing; and
    (iii) a sample core of the subterranean formation is within the circular housing, the outer wall of the sample core being adjacent to the inner wall of the housing and wherein the bottom of the sample core is adjacent to the base plate
  wherein the cementitious slurry is introduced into the housing between and the sample core; the vertical rod
  (b) forming a testing apparatus by positioning a test plate onto the top of the circular housing, the test plate having a flat surface and a through-hole and wherein the upper portion of the vertical rod extends through the through-hole;
  (c) subjecting the testing apparatus to heat at a temperature and for a time sufficient for the cementitious slurry to set in the testing apparatus;
  (d) removing the test plate and the base plate from the circular housing;
  (e) applying a testing plate onto the bottom of the housing, the testing plate having a through-hole for passing the bottom of the vertical rod through the through-hole and further wherein the testing plate has a cavity surrounding the through-hole, the sample core resting within the cavity;
  (f) applying a push rod over the top of the vertical rod, applying pressure onto the push rod and measuring the maximum force required to break the bond between the set cement and the sample core; and
  (g) determining the shear bond strength between the set cement and the sample core by dividing the maximum force by the surface area of the vertical rod in contact with the set cement.

21. The method of claim 20, wherein the amount of pressure applied in step (f) is between from about 2,500 to about 5,000 lbs/min.

22. The method of claim 20, wherein the outer diameter of the sample core is between from about 2 to about 6 inches.

23. The method of claim 20, wherein the thickness of the sample core is from about 0.375 to about 2 inches.

24. The method of claim 20, wherein the inner diameter of the sample core is between from about 2.0 to about 2.5 inches.

25. The method of claim 20, wherein the test plate and the testing plate are the same, the test plate having a second surface having a cavity for receiving the sample core.

26. A method of pre-determining the shear bond strength of a cement mix prior to pumping a cementitious slurry containing the cement mix between a pre-selected subterranean formation penetrated by a wellbore and casing within the wellbore, the method comprising:
  (a) introducing a portion of the cementitious slurry into a testing apparatus, the testing apparatus comprising:
    (i) a circular housing;
    (ii) a base plate having a recessed area;
    (iii) a vertical rod which extends from the recessed area of the base plate past the uppermost portion of the circular housing
  wherein a sample core of the pre-selected subterranean formation is placed between the inner wall of the circular housing and the vertical rod, the cementitious slurry being introduced into the testing apparatus between the sample core and the vertical rod;
  (b) forming a testing apparatus by positioning a test plate onto the top of the circular housing, the test plate having an opening through which the uppermost portion of the vertical rod extends;
  (c) subjecting the testing apparatus to heat at a temperature and for a time sufficient for the cementitious slurry to harden in the testing apparatus;
  (d) removing the test plate and the base plate from the circular housing;
  (e) applying a testing plate onto the bottom of the housing, the testing plate having a through-hole for passing the bottom of the vertical rod through the through-hole and further wherein the testing plate has a cavity surrounding the through-hole, the sample core resting within the cavity;
  (f) applying a push rod over the top of the vertical rod, applying pressure onto the push rod and measuring the maximum force required to break the bond between the set cement and the sample core; and
  (g) determining the shear bond strength between the hardened cement and the sample core by dividing the maximum force by the surface area of the vertical rod in contact with the hardened cement wherein the shear bond strength of step (g) approximates the shear bond strength of the cement mix, when hardened, between the subterranean formation and the hardened cement.

27. The method of claim 26, wherein the amount of pressure applied in step (f) is between from about 2,500 to about 5,000 lbs/min.

28. The method of claim 27, wherein the outer diameter of the core is between from about 2 to about 6 inches.

29. The method of claim 27, wherein the test plate and the testing plate are the same, the test plate having a second surface having a cavity for receiving the sample core.

* * * * *